United States Patent [19]

Matlock

[11] 4,173,885
[45] Nov. 13, 1979

[54] STANDARD SURFACE ASSEMBLY FOR CALIBRATING A VARIABLE SPEED FRICTION TESTER

[76] Inventor: Tony L. Matlock, 4026 Greenleaf St., Raleigh, N.C. 27606

[21] Appl. No.: 945,874

[22] Filed: Sep. 26, 1978

[51] Int. Cl.² ............................................. G01L 25/00
[52] U.S. Cl. .......................................... 73/1 R; 73/8; 73/9; 73/146
[58] Field of Search ......................... 73/1 R, 8, 9, 146

[56] References Cited

U.S. PATENT DOCUMENTS 3,721,115   3/1973   Kearns ....................................... 73/9

FOREIGN PATENT DOCUMENTS 2326954   5/1973   Fed. Rep. of Germany ................. 73/8

*Primary Examiner*—Donald O. Woodiel

*Attorney, Agent, or Firm*—Mills & Coats

[57] ABSTRACT

The present invention relates to a standard surface assembly that may be used in conjunction with a pendulum type variable speed friction skid tester for calibrating the same. The standard surface assembly includes a standard surface specimen, such as aluminum oxide, and, in use, is positioned below a pendulum swing arm with a rubber tire secured about the lower remote end thereof. The standard surface assembly is positioned with respect to the pendulum such that the rubber tire passes generally tangential to the upper surface thereof, and because the rubber tire is locked it will skid across the upper surface of the standard surface. For any particular swing of the pendulum arm, the energy lost in friction by the skidding wheel against the standard surface is known and consequently the variable speed friction tester can be calibrated to reflect this energy loss.

9 Claims, 3 Drawing Figures

STANDARD SURFACE ASSEMBLY FOR CALIBRATING A VARIABLE SPEED FRICTION TESTER

The present invention relates to instrumentation and testing devices, and more particularly to a standard surface assembly for calibrating a variable speed friction skid tester of the pendulum type utilized to determine the effective skid resistance of roadway pavements.

BACKGROUND OF INVENTION

The effective skid resistance of roadway pavements and surfaces is obviously a very important characteristic of the roadway surface, especially in terms of safety. Thus, there has been and continues to be a need for testing devices to test the effective skid resistance of a roadway pavement or surface or to test pavement specimens being developed.

At North Carolina State University in Raleigh, N.C., a pavement testing device has been developed and this is referred to as a variable speed friction skid tester, and is of the pendulum type. Basically the variable speed friction tester includes a pendulum with a rubber tire secured to a remote lower end thereof. In use, the pendulum is lifted to one side of its pivot point and allowed to swing past a pavement surface disposed in the pendulum's swing path such that the rubber tire passes generally tangential thereover. Because the wheel is locked in at least one direction, it contacts the pavement surface and skids thereover. By measuring the magnitude of the pendulum's movement past the pavement surface, one can determine the energy lost in friction due to the skidding and sliding movement of the rubber tire over the pavement, and this can be converted to a measurement that represents the effective skid resistance of the pavement being tested. Such a tester is suitable for laboratory test on pavement samples as well as actual field tests on highway surfaces.

The variable speed friction tester being referred to above enables one to predict the effect of the vehicle's speed on the skid resistance of wet pavements and to determine the effective skid resistance of actual pavement surfaces.

But with the variable speed friction tester and other conventional skid testers such as the conventional skid trailer and the British portable tester, individuals utilizing the testing devices have found it difficult to calibrate the various test machines and consequently the results of such tests sometimes lack total meaning and consequently cannot be totally understood, appreciated and used in determining the real effective skid resistance of a pavement surface. Thus, there exists a real need for a standard surface for calibrating skid testing devices.

SUMMARY OF INVENTION

The present invention relates to a standard surface assembly that can be used to calibrate testing devices that are used to determine the effective skid resistance of a pavement or highway surface. In particular, the standard surface assembly of the present invention is adapted to be used in conjunction with the pendulum type variable speed friction skid tester of the character referred to above.

Forming a part of the standard surface assembly is a standard surface material or specimen, such as aluminum oxide, that is characterized by an open porous type structure, of a generally medium hardness that is hard enough not to easily be worn by a rubber tire passing thereover, and which is easily duplicated by modest quality control techniques to allow the same to be reproduced time after time.

Basically reviewing the structure of the standard surface assembly, the same includes a base plate with a holder for receiving and supporting the standard surface sample or specimen, and wherein the standard surface assembly is provided with purging means in the form of a low pressure water supply that is directed through the base plate and through the generally porous standard surface material so as to continually purge the same of foreign material, such as rubber particles, such that such foreign material does not affect the test measurements being made.

It is, therefore, an object of the present invention to provide a standard surface assembly including a standard surface for calibrating testing devices that determine effective skid resistance of a highway pavement or surface.

Another object of the present invention is to provide a standard surface assembly of the type referred to above that is particularly adapted to be used to calibrate a pendulum type variable speed friction tester.

In addition, another object of the present invention resides in the provision of a standard surface assembly for a variable speed friction skid tester wherein the standard surface and standard surface assembly is relatively inexpensive, is easy to reproduce, has an indefinite life and allows a friction skid test device to produce reliable and repeatable data that is consistent.

A further object of the present invention is to provide a standard surface assembly of the character described above wherein the surface characteristic of the standard surface will remain generally constant despite extensive use and the tendency for worn areas to develop.

Still a further object of the present invention resides in the provision of a standard surface assembly of the character described above that is provided with purging means for continuously purging the standard surface material of foreign material, such as rubber particles, in order that the composition and make-up of the standard surface material remains generally constant so as to yield reliable and repeatable data.

Another object of the present invention is to provide a standard surface assembly of the basic character described above that is easily duplicated and which can be reproduced with standard quality control techniques.

Other objects and advantages of the present invention will become apparent from a study of the following description and the accompanying drawings which are merely illustrative of the present invention.

DESCRIPTION OF PREFERRED EMBODIMENT

Figure 2:
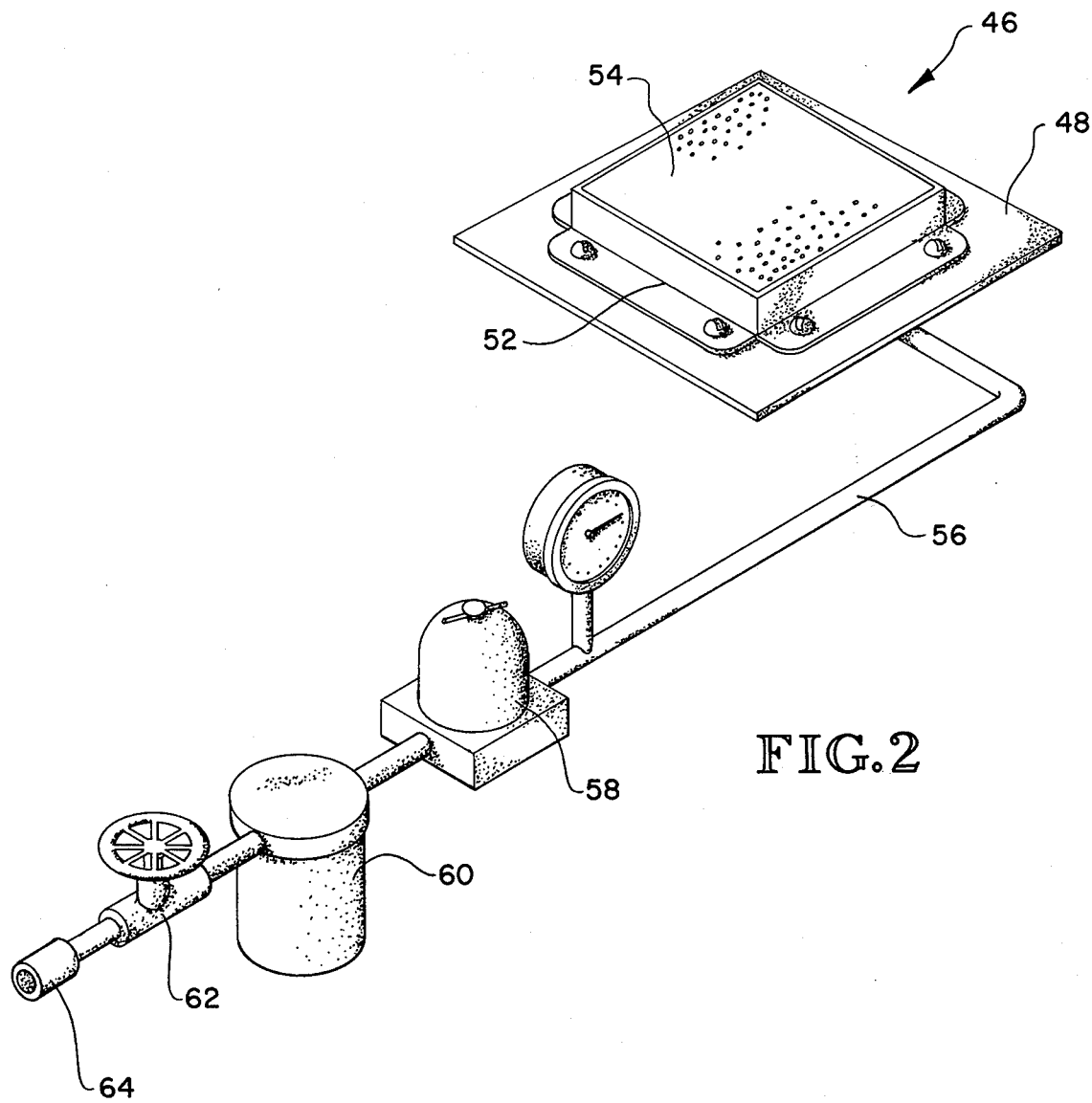
FIG. 2 is a perspective view of the standard surface assembly of the present invention that is adapted to calibrate a skid tester of the pendulum type shown in FIG. 1.
Figure 3:
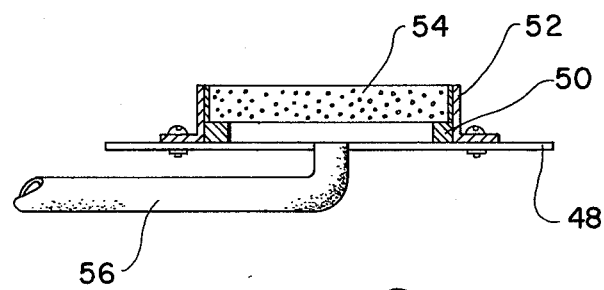
FIG. 3 is a cross sectional view of the standard surface assembly shown in FIG. 2.

The present invention entails a standard surface assembly indicated generally by the numeral 46 in FIG. 2 for calibrating a skid test device. Before discussing the standard surface assembly 46 in detail, a general discussion of a skid test device of the pendulum type is in order, with the understanding that such is intended to give a general structural understanding and appreciation of skid test devices and the basic function thereof.

Figure 1:
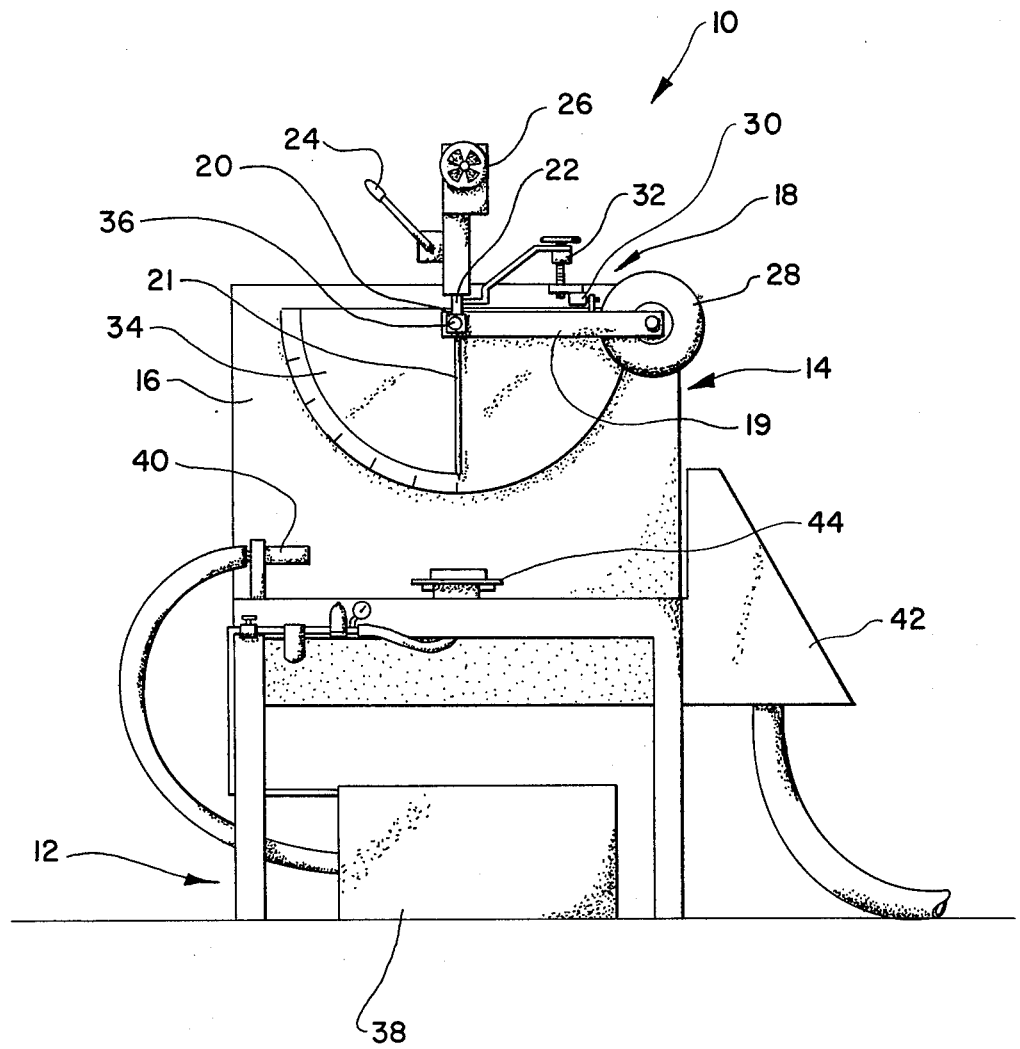
FIG. 1 is a front elevational view of a variable speed friction skid tester of the pendulum type.

In this regard, a variable speed friction skid tester of the pendulum type is shown in FIG. 1 and indicated generally by the numeral 10. Viewing the variable speed friction tester 10, it is seen that the same includes a floor stand 12 that is adapted to support thereabove a tester proper indicated generally at the numeral 14.

The tester proper 14 includes a back frame structure 16 having a pendulum assembly 18 secured thereto. Pendulum assembly 18 comprises an elongated pendulum arm 19 swingably mounted within a carrier frame 20 that is secured to the lower end of a vertical adjustment post 22. Vertical adjustment post 22 is contained within a vertical adjustment assembly and is adapted to be moved up and down therein by a lift handle 24 in a conventional manner, and wherein there is provided a locking assembly 36 that is adapted to secure and hold the vertical adjustment post 22 in a selected position. As will become apparent from subsequent portions of this disclosure, the entire pendulum assembly 18 can be adjusted vertically with respect to the frame structure 16 of the tester proper 14 during the testing of a pavement surface.

Secured to the lower remote end of the pendulum arm 19 is a rubber wheel or tire 28 that includes a ratchet mechanism that effectively locks the wheel for counterclockwise directional movement while allowing the same wheel to rotate clockwise as viewed in FIG. 1. As will become apparent, this assures that as the pendulum assembly 18 swings from right to left, as viewed in FIG. 1, that the wheel 28 will skid across a surface being tested. The tire 28 may preferably be a slick, smooth no pattern tread tire, with a 2-ply rating construction of nylon fabric.

Continuing to refer to the tester proper 14, it is seen that the same includes a pendulum latch assembly, indicated generally by the numeral 30, that includes a vertical adjustment mechanism 32. The pendulum latch assembly 30 is adapted to hold the pendulum arm 19 in a raised position and to release the pendulum arm 19 in response to the operator actuating a release button or the like that effectively frees the pendulum arm 19 from the latch assembly 30 such that the pendulum arm readily falls from an upper raised position.

Disposed adjacent frame structure 16 of the tester proper 14 is a VSN (variable speed number) indicator scale that is utilized to determine the magnitude of movement of the pendulum arm 19 during the test of a pavement surface. VSN indicator scale 34 can be adjusted about an axis that extends generally parallel to the swinging axis of the pendulum arm 19, and, therefore, there is provided an adjustment lock 36 for securing the VSN indicator scale in a stationary and level position with respect to frame structure 16 of the tester proper 14.

A pointer 21 is rotatively mounted adjacent said VSN scale 34, and is particularly frictionally mounted such that it remains in any position about the scale when left free. The pendulum assembly 18 includes a carrier tab (not shown) that is adapted to engage the pointer 21 and to swing the same right to left, as viewed in FIG. 1, during the respective test swings. Thus the pointer 21 functions to indicate the magnitude of movement of the pendulum arm 19 on the VSN scale 34.

In the ordinary use of such the skid testing device 10, a variable pressure water supply system 38 is provided to supply a flow of water, under pressure, across the specimen or sample of pavement being tested and this in effect corresponds to the variable vehicle speed or velocity in such tests. Therefore, the effect of vehicle velocity is introduced by the water supply system 38, including a nozzle 40 which projects the supply of water under pressure between the wheel 28 and the pavement surface being tested. In order to collect the water being utilized, associated with the floor stand 12 is a water collector assembly 42 that is adapted to receive the water being dispersed and to collect the same in a container or to recirculate the same back to the water supply system 38.

Formed about the frame structure 16 in the swinging path of the pendulum 19 and wheel 28, there is provided a specimen holder assembly 44 that is adapted to receive an actual pavement specimen or even a laboratory specimen or the like.

Details of the test method will not be dealt with herein, but a brief discussion is in order. In this regard, the tester proper 14 can be positioned and leveled on a roadway pavement for direct testing of the same, or can be as illustrated in this application positioned and leveled on the floor stand 12. The vertical position of the pendulum is adjusted to provide a specified normal load between the tire or wheel 28 and the pavement being tested. The water supply system 38 is adjusted to where the nozzle pressure is at a desired level to represent the chosen velocity variable.

With the pendulum arm 19 and the pointer 21 in a horizontal starting position, water through the nozzle 40 is directed onto the pavement surface being tested, and the pendulum arm is activated by releasing the same from the pendulum latch assembly 30. This enables the pendulum arm 19 and tire wheel 28 to swing downwardly, from right to left as viewed in FIG. 1, to contact the test surface and swing upward to where the pendulum arm 19 stops and starts the return swing. Because the pointer 21 is carried by the pendulum arm 19, the pointer 21 remains stationed at the highest point of travel of the pendulum arm 19. The pendulum arm 19, on the other hand, returns by swinging left to right, and the operator is positioned so as to catch the pendulum as it swings past the test pavement. Once the pendulum arm is caught, it is then returned to the starting position and adapted so as to be held by the pendulum latch assembly 30.

The VSN indicator scale represents the frictional property obtained by the tester 10 relative the particular pavement or surface being tested. It is appreciated that the VSN, or variable speed number can be used to determine the energy loss in friction by the skidding wheel 28 passing over the pavement surface being tested, and from this, the effective skid resistance of the pavement or pavement's surface can be determined.

The above discussion refers to a variable speed friction skid tester of the pendulum type. The specifics of the tester design and method of use is not presented herewith because such is not per se material to the present invention and in addition skid testers of this type and of the trailer type are known in the prior art, and in fact, are being utilized by North Carolina State University and the North Carolina Department of Transportation.

With skid testers and particularly the pendulum type variable speed friction tester, one particular problem is found in calibrating the testing machine. Besides adjustments needed in the tester proper 14, the rubber tire 28 is a critical variable and often the wheel must be conditioned and properly worn in order to obtain accurate, reliable and consistent results. Thus, there is a need for a standard surface assembly including a standard surface sample for use with the variable speed friction tester 10 in order to calibrate the same, and to particularly check the tire 28 to make sure that it is properly conditioned to give accurate and meaningful results.

Now turning to FIG. 2, the standard surface assembly 46 of the present invention is shown therein and indicated generally by the numeral 46. Viewing the standard surface assembly 46 in detail, it is seen that the same includes a generally flat base plate 48 and a specimen or pavement sample holder 52 that is adapted to be secured to base plate 48. A spacer 50 is disposed generally between holder 52 and the base plate 48. Contained within holder 52 is a standard surface 54 that is supported above base plate 48 and in particular is disposed such that the spacer 50 defines an open area between the lower portion of the standard suface 54 and the plate 48.

Plumbed into the side of base plate 48 opposite the standard surface 54 is a fluid or water inlet line 56 that includes a pressure regulator 58, a filter 60 and a globe valve 62. The water inlet line 56 is provided with a hose adapter coupling 64 in order that the same can be connected to a hose pipe or the like that is in turn connected to a water supply.

Referring to the standard surface 54, in a preferred embodiment of this invention, the standard surface is comprised of an aluminum oxide specimen, but it is understood that other materials exhibiting the characteristics and properties of aluminum oxide of the particular character described herein, could be utilized. For example, silicon carbide could also be used as a standard surface.

With respect to the aluminum oxide material utilized as the standard surface or the standard specimen 54, the same would preferably have a medium hardness, a grain size of approximately 60 grit, and a vitrified bond structure. Of particular significance is the fact that in the preferred embodiment, the aluminum oxide standard surface 54 would have an open or porous structure that would allow water to move therethrough.

In the way of a summary, the aluminum oxide standard surface 54 of a preferred type composition would be hard enough that it is not easily worn by a rubber tire skidding thereover, sufficiently porous to allow water under low pressure (0–100 psig) to pass through it, would be easily duplicated with modest quality control techniques so as to be reproducible, and finally would be of a character and include properties that would simulate a medium slick pavement.

In the case of the aluminum oxide standard surface 54, one very significant property thereof is the property that the same is essentially self-rejuvenating. That is, when the member and size of worn areas across the upper exposed surface increases, this increases the interference or friction, and consequently in the end this results in an increase in the force acting on the grain. Over a period of time, this force becomes large enough to either: (1) exceed the sheer strength of the worn grain and fracture it so as to expose new frictional edges; or (2) exceed the bonding strength of the standard surface material and tear the grain away from the stone, so as to expose new unworn grain.

A second unique and most significant feature of the aluminum oxide standard surface 54 is that the structure is porous in order to allow water to pass therethrough. Thus, with the standard surface assembly 46, a supply of water is directed through the inlet line 56 and forced upwardly through the standard surface 54, at low pressure, generally approximately 10 psig, such that any foreign material, such as rubber particles deposited by the skidding wheel 28, is forced out of the surface and away from the upper test area of the standard surface 54. Consequently, the water supply being directed through the standard surface 54 tends to purge the same and to maintain the character of the upper surface and the material of the standard surface 54 in a pure state.

Therefore, in use, the standard surface assembly 46 can be positioned about the floor stand 12 in the same general location as that normally assumed by a pavement surface sample being tested. Then, by adjusting the variable speed friction skid tester 10 in essentially the same manner as is done when actually performing a test, and then by actually swinging the pendulum arm 19 and associated rubber tire 28 across the standard surface 54, then the entire variable speed frictional skid tester 10 can be calibrated so as to give accurate, reliable and repeatable results. It is appreciated that in the present invention the standard surface assembly is relatively simple and inexpensive, but is reliable and effective to give the precision necessary to calibrate a skid pavement tester and particularly the type of skid tester known as the variable speed pendulum type.

The terms "upper", "lower", "forward", "rearward", etc., have been used herein merely for the convenience of the foregoing specification and in the appended claims to describe the standard surface assembly for calibrating a variable speed friction tester and its parts as oriented in the drawings. It is to be understood, however, that these terms are in no way limiting to the invention since the standard surface assembly for calibrating a variable speed friction tester may obviously be disposed in many different positions when in actual use.

The present invention, of course, may be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. In a variable speed friction tester for testing pavement surfaces and determining the effective skid resistance thereof of the type including a frame structure with a pendulum type swing arm having a rubber wheel secured to one end and locked in at least one direction in order that the wheel will skid over an underlying surface during a test swing of the pendulum, the improvement comprising a standard surface assembly for calibrating said variable speed friction tester, said standard surface assembly including: base means adapted to be secured about the frame structure of said variable speed frictional tester and disposed such that during the testing operation said pendulum will swing thereover; a standard surface material secured about said base means and exposed such that the rubber wheel of said variable speed friction tester will engage the same as the pendulum is swung across said base means during the testing operation, and wherein said standard surface material is sufficiently porous to allow fluid to move therethrough; and means associated with said base means for directing fluid through said standard surface material for purging the same of foreign material such as rubber particles deposited by the rubber wheel.

2. The standard surface assembly for said variable speed friction tester of claim 1 wherein said base means includes a generally flat plate and a surface holder normally secured to said plate and adapted to contain and hold said standard surface material about said base means.

3. The standard surface assembly for said variable speed friction tester of claim 2 wherein said base means further includes a spacer secured between said generally flat plate and said surface holder so as to define an open area between said standard surface material and said plate.

4. The standard surface assembly for said variable speed friction tester of claim 3 wherein said means for purging the standard surface material includes a fluid inlet line plumbed into said plate about the side thereof opposite said standard surface material and wherein said inlet line is adapted to be connected to a fluid source that is capable of delivering fluid such as water, under pressure, to said plate and through the standard surface material supported thereabout.

5. The standard surface assembly for said variable speed friction tester of claim 4 wherein said standard surface material includes a surface material of aluminum oxide.

6. In a variable speed friction tester for testing pavement surfaces and determining the effective skid resistance thereof of the type including a frame structure, a swingably mounted pendulum having a rubber wheel secured to a remote end thereof and normally locked to prohibit rotation in at least one direction, and measuring means for determining the energy lost in friction when said locked wheel contacts a pavement surface during the swing of said pendulum, the improvement comprising a standard surface assembly adapted to be mounted below the normal swing path of said pendulum for engagement with the wheel thereof for calibrating said variable speed friction tester, said standard surface assembly including a base plate having a holder secured to one side thereof; a standard surface pavement material secured within said holder and wherein said standard surface material is sufficiently porous to allow water to be forced therethrough; and an inlet water line plumbed into the other side of said plate opposite said standard surface material; and means for directing water under relatively low pressure through said inlet line and vertically through said standard surface material so as to purge foreign material, such as rubber particles from said rubber wheel, from said standard surface material supported within said holder.

7. The standard surface assembly for said variable speed friction tester of claim 6 wherein said standard surface material includes an aluminum oxide sample.

8. The standard surface assembly for said variable speed friction tester of claim 7 wherein said aluminum oxide sample includes a grain size of approximately 60 grit, is of a generally medium hardness, and wherein the bond is vitrified.

9. A standard surface assembly for calibrating a variable speed friction skid tester of the pendulum type, said standard surface assembly including a base plate having a holder secured to one side thereof, a porous standard surface secured within said holder and wherein said standard surface is sufficiently porous to allow water to be forced therethrough; an inlet water line plumbed into the other side of said plate opposite said standard surface; and means for directing the water under relatively low pressure through said inlet line and vertically through said standard surface so as to purge foreign material, such as rubber particles, from said standard surface.

* * * * *